United States Patent [19]
Gowan, Jr. et al.

[11] Patent Number: 6,090,401
[45] Date of Patent: Jul. 18, 2000

[54] STABLE FOAM COMPOSITION

[75] Inventors: Walter G. Gowan, Jr., Dublin, Ohio; Richard D. Fegley, Bethlehem, Pa.; Daniel McTeigue, North Whales, Pa.; Thomas E. Sox, Ambler, Pa.

[73] Assignee: McNeil-PPC, Inc., Skillman, N.J.

[21] Appl. No.: 09/282,859

[22] Filed: Mar. 31, 1999

[51] Int. Cl.[7] .............................. A61K 47/00; A61K 9/20; A61K 9/16; A61K 9/50
[52] U.S. Cl. .................... 424/439; 424/490; 424/493; 424/497; 424/464; 424/501
[58] Field of Search ................... 424/490, 439, 424/464, 493, 497, 501; 514/84.1

[56] References Cited

U.S. PATENT DOCUMENTS

| | | | |
|---|---|---|---|
| 4,251,561 | 2/1981 | Gejewski | 426/571 |
| 4,306,059 | 12/1981 | Yokobayashi et al. | 536/1 |
| 4,401,508 | 8/1983 | Ritt | 156/659.1 |
| 4,714,620 | 12/1987 | Bunick et al. | 426/572 |
| 4,803,077 | 2/1989 | Mitsuhashi et al. | 424/439 |
| 5,126,160 | 6/1992 | Giddey et al. | 426/564 |
| 5,352,709 | 10/1994 | Tarrant et al. | 521/84.1 |
| 5,393,528 | 2/1995 | Staab | 424/436 |
| 5,451,419 | 9/1995 | Schwab et al. | 426/564 |
| 5,457,163 | 10/1995 | Hartranft et al. | 521/109.1 |
| 5,458,884 | 10/1995 | Britton et al. | 424/435 |
| 5,462,760 | 10/1995 | Serpelloni et al. | 426/572 |
| 5,523,106 | 6/1996 | Gimmier et al. | 426/549 |
| 5,660,954 | 8/1997 | Suga et al. | 430/1 |

*Primary Examiner*—Thurman K. Page
*Assistant Examiner*—Susan Tran

[57] ABSTRACT

The present invention provides a quick dissolving, readily broken substrate suitable for the addition of pharmaceutical agents for oral administration. A method for making the substrate is also disclosed.

24 Claims, No Drawings

STABLE FOAM COMPOSITION

FIELD OF THE INVENTION

The present invention relates to dried foam compositions, hereinafter referred to as foam tabs, that may be used as foodstuffs, or alternatively may be used as vehicles for the oral delivery of pharmaceuticals, nutritional compounds, or other bioactive materials. This invention also incorporates a process for making these compositions.

BACKGROUND OF THE INVENTION

Convenience of use is an important aspect in the development of pharmaceutical and nutritional dosage forms. This convenience results in improved user compliance with the desired dosing regimen. A particular aspect of convenience of oral dosage forms is the ability to consume these without access to water or other liquids to aid in swallowing. This benefit is especially important to those who are travelling or who do not have ready access to liquids. Preferred portable dosage forms are chewable products, or products that dissolve readily in the mouth without chewing. Not surprisingly, great effort has been expended in the pharmaceutical and nutritional industries in the development of these convenient dosage forms. The intent of the current invention is to achieve these objectives with an economical, versatile manufacturing process.

U.S. Pat. No. 4,251,561, incorporated herein by reference, describes the preparation of a stable aerated confection which is prepared by forming a confection melt consisting of dextrose and a protein material. The melt, which is heated to about 75 to 110° C., is aerated by the injection of gas under pressure. The foam may be extruded from a die, and the extruded material cut into desired lengths after solidification of the sugar/protein foam. Examples of proteins that may work in this application include gelatin, soy protein, and egg albumin. Candy products may be formed by the addition of appropriate flavors.

U.S. Pat. No. 4,714,620, incorporated herein by reference, discloses the manufacture of various aerated confectionery compositions. The process consisted of making a frappe (including gum arabic, gelatin, hydrogenated starch hydrolysate, and hydroxypropylmethylcellulose (HPMC)). A syrup (including hydrogenated starch hydrolysate, mannitol, and optionally a thickening agent) is prepared by cooking at 180° C. The syrup is then cooled to about 130° C. and added to the frappe by mixing at low speed. Other materials, such as fat, flavor, or color could optionally be added during the mixing operation. The aerated product could be cut or formed into final shapes, and then wrapped. The patent does not disclose the addition of medicaments, particularly coated particles of medicaments, to these compositions, presumably because the high temperatures involved in the manufacture of these compositions would damage the integrity of the coating of any coated drug particles added during manufacture, thereby vitiating the taste masking benefits obtained with these coated particles.

According to U.S. Pat. No. 5,393,528, a foam for the vaginal delivery of active materials can be prepared by mixing HPMC, glycerin, and the active ingredient, and introducing nitrogen gas while mixing to form a frothy foam. The mixture is then cast as a foamed film on a solid surface. Alternatively, the frothy foam can be dispensed into a mold to yield a formed device such as a diaphragm. Polyethylene oxide or polyvinyl alcohol may be used in place of HPMC as a foaming agent. The patent does not discuss the oral consumption of these foams, or the incorporation of coated particles of active ingredient in these foams.

A foamed ibuprofen-containing dosage is disclosed in German patent application 19635676. A mixed copolymer of N-vinylpyrrolidone and vinyl acetate is melted with ibuprofen. The melt is impregnated with carbon dioxide gas while being passed through an extruder. The carbon dioxide expands to yield bubbles impregnated in the melt after it exits from the extruder. The ibuprofen in this foam was co-dissolved with polymer, and therefore the foam would probably impart the unpleasant taste of ibuprofen to the oral cavity when the foam was chewed or allowed to dissolve in the mouth. Additionally, the entrapped bubbles of carbon dioxide could impart an additional bitter taste to foam.

Despite the disclosures of the prior art there is an ongoing need to prepare good tasting, quick dissolving matrices for the delivery of pharmaceutically active ingredients.

SUMMARY OF THE INVENTION

The present invention provides edible dried foam compositions comprising a polymeric foaming agent selected from proteins and cellulose derivatives; optionally a non-cellulosic polysaccharide; and preferably including a pharmaceutically active ingredient, wherein the bulk density of the dried foam is generally less than about 0.40 grams/cubic centimeter. The present invention also provides a method for making the compositions which preferably includes the use of an entrained gas. The entrained gas provides homogeneously dispersed bubbles in the dried foam tab, and in a preferred embodiment the foam tab is formed in situ in a mold suitable for shipping the product.

DETAILED DESCRIPTION OF THE INVENTION

Suitable materials for the polymeric foaming agent of the present invention are well known in the art, and include proteins, protein hydrolyzates, cellulose derivatives or naturally occurring macromolecules. Suitable protein hydrolyzates include, casseinate, whey and vegetable proteins; gelatin, egg whites and mixtures thereof. Preferred proteins are casseinates derived from spray dried milk products. Similarly, suitable cellulose derivatives useful in the present invention include methyl cellulose, hydroxymethyl cellulose, hydroxypropylmethylcellulose, hydroxypropyl cellulose and other substituted cellulose derivatives, see for example U.S. Pat. No. 5,576,306, herein incorporated by reference. Naturally occurring macromolecules include albumen and casein. Mixtures of polymeric foaming agents may also be employed.

In a preferred embodiment, the compositions of the present invention also include a non-cellulosic polysaccharide, of either natural or synthetic origin. Natural polysaccharides are preferred including xantham gum, agar and especially preferred is carrageenan.

The level of polymeric foaming agent in the foam tab can be up to essentially the entire weight of the foam tab matrix, greater than 99 weight percent, before additional ingredients such as excipients, preservatives, flavorings etc., are included. More preferably the foam tab matrix is comprised of the polymeric foaming agent and the non-cellulosic polysaccharide. The weight ratio of the polymeric foaming agent to the non-cellulosic polysaccharide is generally greater than about 5.5 to 1; preferably from about 7.5 to about 30 to 1; and most preferably from about from about 9 to about 20 to 1.

The polymeric foaming agent and non-cellulosic polysaccharide are admixed in a solvent. The solvent is any suitable solvent for human consumption, with water, particularly deionized water most preferred. In a preferred embodiment the pharmaceutically active ingredient is not admixed with the polymeric film forming agent and non-cellulosic polysaccharide until the foam tab is formed after drying.

The density of the foam tabs prepared by the present invention range from about 0.15 grams /cubic centimeter (g/cc) to about 0.35 g/cc; preferably from about 0.20 to about 0.30 and most preferably from about 0.22 to about 0.28 g/cc with an average value of about 0.26 g/cc.

The solvent content of the foam tabs after drying is less than about 3 weight percent; preferably less than 2 and most preferably from about 1.0 to about 1.6 weight percent.

One or more pharmaceutical or nutritional materials may be dispersed into this foam. The foam is then dried to yield a dosage form that may be chewed, or that readily dissolves in the mouth without chewing. The foam may be dispensed into molds before drying to yield uniform dosage forms. Alternatively, the foam may be dried in large sheets or blocks, and the dried foam is subsequently subdivided into individual dosage units. Materials useful as pharmaceutical actives or nutritional supplements may be added to the solution that is used to generate the foam, or they may be added to the foam after it is generated. The addition of drugs to the dried dosage forms has several potential advantages. First, the amount of drug added can be carefully controlled. This overcomes potential variations in the weight of the dosage forms produced by the foam generating and dispensing process, which could result in variations in the drug in the amount of drug delivered. Also, this addition of drug as a solution or dispersion in a solvent to the dried foam dosage unit allows the use of drugs that are unstable in water. Finally, the addition of drug directly to the dried foam dosage form allows the production of dosage units containing different levels of drugs, or alternatively, different drugs can be added to various portions of a single batch of dried dosage units.

The pharmaceutical actives or nutritional supplements often have a bitter or unpleasant taste, rendering undesirable products made with these materials that are intended or chewing or dissolving in the mouth. Therefore, some procedure for masking the unpleasant taste of these materials may be incorporated into the current invention. Especially preferred is the incorporation of particulate pharmaceutical actives or particulate nutritional supplements which have been coated with a lipid or polymer film. The lipid or polymer film protects the active or supplement from dissolving in the mouth, thereby masking the taste of the material. These coated particles may be introduced into the foam at any point prior to drying. However, addition of these particles just before the foam is dispensed for drying is preferable, since this minimizes the amount of time that the particles are exposed to high levels of moisture present in the undried foam. These particles are preferably added after the vigorous agitation or mixing process that is needed to entrain gas bubbles in the foam. This agitation or mixing may result in fracture or breakage of the coated particles. Additionally, the longer duration of exposure of the coated particles to the high moisture content of the undried foam increases the amount of material in the coated particles that dissolves and leaches into the liquid foam portion.

A preferred method consists of first drying the foam, and then adding the pharmaceutical or nutritional material as a liquid or solution that does not substantially collapse the foam. This approach is especially preferred for materials that are active at very low doses, or are sufficiently volatile that they would be lost during the process of drying the wet foam. Nicotine is an example of a material that may advantageously be incorporated into the foam in this manner. One additional benefit of adding the active material to the foam after drying is that the dosing amount can be carefully controlled. When active materials are added to the foam before drying, the amount of active material may be affected by variations in the amount of foam that is incorporated into the dosage unit, or by non-uniformity of the active material in the foam before drying.

Examples of pharmaceutical actives that may be advantageously incorporated as coated particles include acetaminophen, ibuprofen, ketoprofen, naproxen, loperamide, famotidine, cimetidine, ranitidine, diphenydramine, pseudoephedrine, loratidine, aspirin, and ebastine, and pharmaceutically acceptable salts thereof. Other pharmaceutical actives are disclosed in U.S. Pat. No. 5,446,070, the contents of which are hereby incorporated by reference. Examples of nutritional supplements that may be advantageously incorporated as coated particles include niacin, B vitamins, decosahexaenoic acid, conjugated linoleic acid, phytosterols, iron salts, and salts of other essential minerals. Numerous other drugs may be applied to the foam dosage forms in this manner. Drugs that have relatively low therapeutic doses are preferred. Also preferred are drugs that are relatively tasteless, since this approach does not provide taste-masking of the unpleasant taste of the drugs.

The process of preparing foams by mixing a polymer or a mixture of polymers with air or other gas under conditions of vigorous agitation so that gas is entrained as small bubbles is well known. The foams may be created by vigorous agitation of a polymer solution in the presence of air, inert gases and mixtures of gases such as nitrogen, carbon dioxide, helium and the like may be incorporated into the foam. Alternatively, a commercially available foam generating unit may be used. An example are the foamers made by the Oakes Corporation The degree of agitation and gas entrainment must be carefully controlled so as to provide foams of appropriate density. This density control is important in maintaining a uniform weight of the dosage forms created by drying. Drying of the foam results in the creation of a stable solid material. Drying may occur by atmospheric exposure at room temperature or at elevated temperatures in an oven, at temperatures preferably less than 70°, most preferably less than 50° C. Alternatively, drying may be carried out by lyophilization. Foams may be molded or cast into precise shapes before drying. Also, some foams are sufficiently stable so that they can be cut into uniform sections after drying.

Additionally, a sugar or other carbohydrate material may be dissolved in the foam. The sugar or carbohydrate adds additional bulk to the foam after drying, furthermore, the drying and crystallization of the sugar or other carbohydrate provides additional strength to the dried foam. The sugar or other carbohydrate can add sweetness to the dried foam or otherwise improve the organoleptic qualities of the foam. Examples of sugars which may be used include maltose, lactose, sucrose, dextrose, and trehalose, as well as sugar-alcohols, such as mannitol, sorbitol, xylitol, maltitol, and the like. Examples of other carbohydrates include maltodextrin, corn syrup solids, soluble starches and the like.

Other materials may be added to improve the taste or physical properties of the dried foam. Flavor may be added; examples of flavors are vanilla, orange, orange cream, strawberry, and raspberry. Additionally, natural or artificial colors may be added. Also, artificial sweeteners may be added; these sweeteners may increase the level of sweetness beyond that obtained by adding sugar to the foam. Examples of artificial sweeteners include sucralose, aspartame, cyclamate, saccharin, and acesulfame and their salts. Various acids may be added to provide a pleasant tartness to the foam. Examples of acids that may be used include citric, malic, tartaric, and 2,4-dihydroxybenzoic acids. Additionally, the incorporation of these acids may be used to decrease the pH of the foam. This is especially desirable for materials such as ibuprofen that are relatively insoluble under acidic conditions. This decreased solubility decreases the amount of ibuprofen that dissolves into the foam, thereby improving the taste of the dried foam.

Additionally, humectant materials may be added to improve the aesthetic properties of the dried foam and decrease the friability of the dried foam. Examples of humectants include glycerol, propylene glycol, and polyglycerol esters. Also, surfactant materials may be added to improve the stability of the foam before or after drying. Examples of desirable surfactants include the TWEEN (ICI Americas) series of substituted sorbitan derivatives.

A large variety of molding materials may be used for the production of uniform foam tabs. In addition to metal molds or trays, conventional blister package materials such as, but not limited to, polyvinyl chloride (PVC) or polyvinylidiene chloride (PVDC) or fluorohalocarbon film (ACLAR available from Allied-Signal) may be used. The interior of the blister cavities may be coated with a release agent such as a silicone preparation. Other suitable surfaces for drying foam tablets include TEFLON-coated sheets, POREX polyethylene sheets, and polystyrene plastic sheets or molds. Release of the dried foam tablets may be enhanced by coating the surfaces with a silicone mold release agent, vegetable oils, lecithin, glycerin or talc prior to deposition of the foam onto these surfaces. Materials such as glycerin serve the purposes of lubricating and softening the foam and conferring flexibility and resistance to friability to the dried dosage forms.

As used throughout the specification liquid forms is understood to include without limitation neat liquids, solutions, suspensions, emulsions, dispersions and the like.

The following examples are provided as specific embodiments of the present invention. Other modifications of this invention will be readily apparent to those skilled in these arts without departing from the scope of the present invention. Unless noted to the contrary all measurements are weight and g is understood to be grams.

EXAMPLE 1

Spray Dried (SD) Caseinate RC-200 (American Casein Company, Burlington, N.J.) (10 g) was added to 100 ml of deionized water and stirred with a laboratory mixer (Jiffy Mixer Co. Inc., Riverside, Calif.) for 20 minutes. Separately, Genugel CJ carrageenan (Hercules Inc., Wilmington, Del.) (1 g) was added to 100 ml of deionized water and stirred with a laboratory mixer for 20 minutes. The two solutions were combined in an 800 ml beaker and the following additional materials were added: Aspartame 0.4 g; Red Dye FD&C 40 0.1 g; Alpine Cream Flavor 0.2 g; Polymer-coated acetaminophen particles (Eurand, Vandalia, Ohio) 38.5 g. Additional deionized water was added to bring the weight of the mixture to 250 g.

Mixing was continued at the highest speed of the laboratory mixer for an additional 30 minutes, with the blade height positioned so that the lower surface of the blade was just beneath the initial liquid surface. This created maximal cavitation (bubble formation). This mixing created a uniform foam of approximately 500 cubic centimeters (cc). The foam was dispensed in 0.59 g aliquots into plastic weigh boats and allowed to dry overnight.

After drying, the solidified foam dosage units were readily removed from the plastic weigh boats by flexing the weigh boats. Each unit contained approximately 80 mg of acetaminophen. The dosage units had a crunchy texture and dissolved quickly in the mouth with chewing. They possessed a slightly bitter taste.

EXAMPLE 2

SD caseinate RC-200 (25 g) was added to about 100 ml of deionized water and stirred with a laboratory mixer for 20 minutes. Separately, Genugel CJ carrageenan (2.5 g) was added to about 100 ml of deionized water and stirred with a laboratory mixer for 20 minutes. The two solutions were combined in an 2 liter beaker and the following additional materials were added: mannitol 25.0 g; aspartame 2.0 g; Alpine Cream Flavor 0.46 g; Red Dye FD&C 40 0.1 g; polymer-coated acetaminophen particles 90.9 g. Additional deionized water was added to bring the total weight of the mixture to 500 g. Mixing was continued with a Jiffy LM blade at the highest speed of the laboratory mixer for an additional 30 minutes, with the blade height positioned to create maximal cavitation. Approximately 1600 cc of stable foam was obtained. The foam was dispensed into weigh boats, dried, and the dosage units were removed as described in Example 1. The dosage units had a fine-grained appearance, and dissolved quickly in the mouth. They had a creamy flavor and were not grainy. The dosage units crumbled between the fingers when a slight pressure was applied.

EXAMPLE 3

The following were added to 31.4 ml of deionized water in a 300 ml beaker: spray dried caseinate RC-200 1.57 g; Carrageenan Genugel CJ 0.157 g; Mannitol 2080 (SPI Polyols, New Castle, Del.)7.52 g; aspartame 0.154 g; Alpine Cream Flavor 0.041 g; Red Dye FD&C 40 0.006 g; Polysorbate 80 (ICI Americas) 0.05 g; glycerol 1.3 g; polymer-coated acetaminophen 9.4 g.

Mixing was performed as described in Example 2. The foam was dispensed into weigh boats and plastic blister cavities for pharmaceutical packaging, and allowed to dry. The dosage units adhered to the weigh boats but could be readily removed from the blister cavities. The dosage units dissolved quite rapidly in the mouth, with good mouthfeel and a pleasant aftertaste.

EXAMPLE 4

The following formulation was combined in a beaker: deionized water 82.0 g; HPMC K35 (Dow Chemical) 2.25 g; HPMC E5 (Dow Chemical) 2.25 g; Carrageenan Genugel CJ (SOURCE) 0.45 g; Mannitol 2080 15.85 g; aspartame 2.04 g; Red Dye FD&C 40 0.01 g; coated ibuprofen particles (source) 26.0 g; citric acid 1.02 g; glycerin 2.0 g; Yellow Dye FD&C 10 0.01 g; orange flavor 0.42 g; Prosweet Powder (Virginia Dare) 0.53 g; Alpine Cream Flavor 1.5 g; stearic acid 0.36 g.

The HPMC and carrageenan were dissolved in the water with a Jiffy mixer before the addition of the remaining ingredients. Mixing was performed as described in Example 2. The foam was dispensed into blister cavities and allowed to dry at room temperature. Dosage units could be readily removed from the blister cavities. The dosage units were uniform, smooth tablets. Each contained approximately 100 mg of ibuprofen. They dissolved in the mouth moderately rapidly, with a pleasing orange flavor.

EXAMPLE 5

The following formulation was prepared: deionized water 41.0 g; HPMC K35 1.125 g; HPMC E5 1.125 g; Carrageenan Genugel CJ 0.225 g; mannitol 2080 7.925 g; aspartame 0.5 g; Red Dye FD&C 40 0.05 g; coated acetaminophen particles 11.5 g; Alpine Cream Flavor 1.5 g; propylene glycol 1.425 g.

The HPMC was dissolved before the addition of the remaining ingredients. Mixing was performed as described in Example 2. Foam was dispensed in two groups of blister cavities. One group was dried at room temperature. The second group was dried for four hours in an oven set at 40 C. Both groups yielded dosage units that were a thick, cake-frosting texture of foam that was slightly elastic. The dosage units were easily removable from the blister cavities, and dissolved quickly in the mouth with a slightly gummy mouthfeel and a slight bitter taste.

EXAMPLE 6

The following formulation was combined in a 250 ml beaker: deionized water 31.4 g; SD Casein RC-200 1.88 g; Carrageenan Genugel CJ 0.157 g; Mannitol 2080 7.52 g; aspartame 0.5 g; Alpine Cream Flavor 0.041 g; propylene glycol 0.5 g; glycerol 1.3 g; coated acetaminophen particles 9.8 g; Red Dye FD&C 40 0.005 g.

The casein and carrageenan were added to the water first, and dissolved with a Jiffy mixer. After dissolution, the speed of the mixer was increased so that foaming occurred. The remaining ingredients except the acetaminophen and dye were added in the above order. After the volume of foam reached about 125–150 cubic centimeter, a Jiffy LM blade was placed in the mixer and the speed of the mixer was adjusted to generate about 200 cc of foam volume. After the desired level of foam was achieved, the acetaminophen and dye were added while mixing continued. Mixing was stopped as soon as the dye was uniformly dispersed in the foam. Aliquots of 0.5 g were dispensed in two groups of blister cavities. One group was dried at room temperature, and the second was dried at 50 C. Dosage units dried at room temperature were firmly adherent to the blister cavity, and could not readily be removed without breaking. In contrast, the dosage units dried at 50 C could be easily removed from the blister as one solid, uniform piece.

EXAMPLE 7

A solution of the following prepared was prepared: deionized water 31.4 g; spray-dried Casein RC-200 1.88 g; Genugel CJ Carrageenan 0.157 g; Mannitol 2080 7.52 g; aspartame 0.5 g; Alpine Cream Flavor 0.041 g; propylene glycol 0.5 g; glycerol 1.3 g; Red Dye FD&C 40 0.005 g.

The above solution was stirred into a foam with a laboratory mixer, and 25 g of calcium carbonate was added. The foam was dispensed in aliquots onto the surface of glass sheets and dried. The foam possessed a very stiff texture, and did not collapse during the drying process. Dosage units dissolved in the mouth quickly, and had a pleasant flavor.

EXAMPLE 8

The following materials were used: deionized water 82.0 g; HPMC K35 2.25 g; HPMC E5 2.25 g; Genugel CJ 0.45 g; Mannitol 2080 15.85 g; aspartame 2.04 g; glycerin 2.0 g; citric acid 1.02 g; orange flavor 0.53 g; Prosweet 0.46 g; Alpine Cream Flavor 1.7 g; calcium carbonate 56.0 g.

HPMC and Genugel were added to the water, and mixed in a 250 ml beaker for 15 minutes. The mixture was then aerated with a laboratory mixer equipped with a standard blade to initiate foam formation. A Jiffy blade was then placed in the mixer, and the remaining ingredients were added in the order provided. The foam was dispensed into plastic blister cavities, and then dried in an oven set at 40 C.

The resulting dosage units consisted of very fine-textured foam that did not collapse during drying. The calcium carbonate content of the dosage forms was 66% on a dry weight basis. The product possessed excellent taste properties.

EXAMPLE 9

| Ingredient | A | B | C | D |
| --- | --- | --- | --- | --- |
| Genugel CJ | 0.45 g | — | 0.45 g | 0.45 g |
| HPMC K35 | 2.25 g | 2.25 g | — | 2.25 g |
| HPMC E5 | 2.25 g | 2.25 g | 2.25 g | — |
| Mannitol 2080 | 11.64 g | 11.64 g | 11.64 g | 11.64 g |
| Deionized Water | 80.0 g | 80.0 g | 80.0 g | 80.0 g |

Foams of the above formulas were prepared by the following procedure: Deionized water was placed in a tall 300 ml beaker (Pyrex No. 1040). The water was stirred with a Jiffy mixer. Each ingredient was added in the order shown. The solution was stirred for 20 minutes after the addition of each ingredient. The mixer was increased to maximum speed 20 minutes after the addition of the last ingredient, and the mixing was continued for 30 minutes. Samples of each mixture were placed in blister cavities and allowed to dry overnight at room temperature.

Formula A yielded dried foams consisting of medium and fine bubbles. Formula B produced dried foams with a slightly crystalline appearance. Formulas C and D yielded foams that suffered substantial collapse during drying.

The compositions of this example can be used to prepare drug-containing dosage forms by applying a drug dissolved or suspended in a solvent to the dried dosage form. Preferably, the solvent or combination of solvents used causes little or no collapse of the foam structure. Residual solvent can be removed from the dosage form by drying at room temperature or in an oven. Alternatively, the solvent may be removed by lyophilization.

For example, nicotine may be dissolved in acetone, and the solution applied to the surface of the dried dosage units of formula A with a micropipet. The final dosage forms preferably contain from 0.1 mg to 1.0 mg of nicotine, depending on the amount of solution applied to the surface of the dosage units.

Nicotine hemisulfate may be dissolved in propylene glycol, and the resulting solution applied to the surface of the dosage units of formula A with a micropipet. The final dosage forms preferably contain from 0.1 mg to 2.5 mg of nicotine, depending on the amount of solution applied to the surface of the dosage units.

The addition of different levels of nicotine to the dried dosage forms can provide the individual who desires to cease smoking with a range of concentrations of nicotine dosage forms. This is especially useful for individuals who desire to use the "step-down" approach for smoking cessation, where decreasing amounts of nicotine are ingested over time as a way of weaning the individual away from nicotine dependence.

EXAMPLE 10

|  | A | B | C |
| --- | --- | --- | --- |
| Deionized Water | 82.0 g | 82.0 g | 82.0 g |
| Glycerol | 2.0 g | 2.0 g | 2.0 g |
| HMPC K35 | 2.25 g | 2.25 g | 2.25 g |
| HPMC E5 | 2.25 g | 2.25 g | 2.25 g |
| Genugel CJ | 0.65 g | 0.65 g | 0.65 g |
| Aspartame | 2.04 g | 2.04 g | 2.04 g |
| Mannitol 2080 | 15.85 g | 15.85 g | 15.85 g |
| Red Dye FD & C 40 | 0.01 g | 0.01 g | 0.01 g |
| Yellow Dye FD & C 10 | 0.01 g | 0.01 g | 0.01 g |
| Citric Acid | — | 1.0 g | 2.0 g |
| Orange Flavor | 0.42 g | 0.42 g | 0.42 g |
| Prosweet | 0.53 g | 0.53 g | 0.53 g |
| Alpine Cream Flavor | 1.5 g | 1.5 g | 1.5 g |
| Coated Ibuprofen | 22.0 g | 22.0 g | 22.0 g |

Foam dosage units were prepared from the above formulas by the following procedure: water and glycerin were added to a 400 ml beaker and stirred at low speed with a Jiffy mixer. HPMC and Genugel were then added, and mixing was continued for 30 minutes until all material dissolved. Mannitol and aspartame were added and the mixture was stirred for about 15 minutes. The mixture was then mixed at fall speed until the foam volume reached about 250 cc. Mixing speed was reduced, and the remaining materials were added. Mixing was continued until the mixture was uniform. Samples were placed in plastic blisters and dried at room temperature.

Dosage units of formula A were dull in appearance and contained dried bubbles of small and medium sizes. In contrast, Samples of formulas B and C were shiny in appearance and consisted of dried foams of bubbles that were small and uniform in size.

EXAMPLE 11

|  | A | B | C |
| --- | --- | --- | --- |
| Deionized Water | 82.0 g | 82.0 g | 82.0 g |
| Glycerol | 2.0 g | 2.0 g | 2.0 g |
| HMPC K100 | 1.125 g | 1.125 g | 1.125 g |
| HPMC E5 | 2.25 g | 2.25 g | 2.25 g |
| Genugel CJ | 0.65 g | 0.65 g | 0.65 g |
| Aspartame | 2.04 g | 2.04 g | 2.04 g |
| Mannitol 2080 | 15.85 g | 15.85 g | 15.85 g |
| FD & C Red 40 | 0.01 g | 0.01 g | 0.01 g |
| FD & C Yellow 10 | 0.01 g | 0.01 g | 0.01 g |
| Citric Acid | 1.02 g | 1.02 g | 1.02 g |
| Orange Flavor | 0.42 g | 0.42 g | 0.42 g |
| Prosweet | 0.53 g | 0.53 g | 0.53 g |
| Alpine Cream Flavor | 1.5 g | 1.5 g | 1.5 g |
| Glycine | — | 2.00 g | 6.00 g |
| Ibuprofen | 21.66 g | 22.00 g | 22.80 g |

Foam dosage units were prepared by the procedure described in Example 10. Dosage units of formulas A and B were similar in appearance, with smaller bubbles at the top of the dosage units than at the bottom. Dosage units of formula C contained larger bubbles. Dosage units of formula C dissolved in the mouth more rapidly than those of formula A, which did not contain glycine.

EXAMPLE 12

Foam dosage units were prepared from the formula provided below by the procedure described in Example 10, except that the addition of 2,4-dihydroxybenzoic acid was just after the addition of glycerol: deionized water 29.57 g; 2,4-dihydroxy-benzoic acid 0.46 g; glycerol 2.24 g; HPMC K3 2.99 g; HPMC E5 1.50 g; Genugel CJ 0.13 g; Mannitol 2080 13.46 g; Alpine Cream Flavor 0.60 g; vanilla 0.50 g; aspartame 0.67 g; coated ibuprofen 19.80 g.

The dosage units had a coarse foam structure with large air pockets. The units dissolved quickly in the mouth, and did not produce the burning sensation in the mouth and throat that is frequently encountered with oral ibuprofen dosage forms. The lack of burn may been resulted from the relative insolubility of ibuprofen because of the acidity imparted to the oral cavity by the dihydroxybenzoic acid. In other experiments, similar levels of citric acid were also found to decrease the amount of burning sensation associated with ibuprofen.

EXAMPLE 13

The following formulation was prepared: deionized water 100.00 g; SD caseinate RC200 5.00 g; citric acid 0.78 g; xantham gum 1.00 g; mannitol 15.85 g; aspartame 2.04 g; glycerin 2.00 g; orange flavor 0.42 g; Prosweet 0.53 g; Alpine Cream Flavor 1.50 g; coated acetaminophen (Eurand) 32.00 g.

The caseinate was added to the water in a 400 ml beaker, and mixed for 5 minutes at low speed with a small propeller blade. Then mixture was mixed at the maximum speed of a Jiffy mixer for 30 minutes. Citric acid was added and the mixing was continued for 5 minutes. Xantham gum was then added, and a large Jiffy blade was installed on the mixer. Mixing was continued at 700 rpm for about five minutes. Mannitol and aspartame were then added and mixing was continued for an additional 15 minutes. Flavors were then added, followed by the coated acetaminophen. The foam was dispensed in 430 mg aliquots onto a silicone-coated plastic surface and allowed to dry. Each dosage unit contained approximately 80 mg of acetaminophen. Dried dosage forms dissolved in the mouth quickly, and had a pleasant flavor.

EXAMPLE 14

The following formulation was prepared: deionized water 289.00 g; HPMC K3 11.50 g; HPMC E5 18.78 g; Carrageenan Genugul CJ 0.96 g; Mannitol 2080 86.21 g; Alpine Cream Flavor 2.64 g; cherry flavor 0.64 g; aspartame 6.64 g; coated ibuprofen 74.14 g.

The ibuprofen had been coated with cellulose acetate and Eudragit E-100 in a 60/40 ration. The polymers represented 26.4% of the weight of the coated particles. Water was heated to 60 C., and HPMC was added. Mixing at low speed (200–500 rpm) was continued for about five minutes. The carrageenan was then added, and mixing was continued until the it dissolved. The remaining ingredients were added while mixing was maintained. The mixture was cooled to 35 C. Mixing speed was increased to 2000 rpm to create cavitation and foaming. After foaming began, mixing speed was decreased and the ibuprofen was added. Mixing was continued for 85 minutes, and aliquots of foam were removed at intervals. The aliquots were diluted into 5 ml of water, and the resulting solution was assayed for dissolved ibuprofen. This provided a measure of the portion of the ibuprofen that leached from the coated particles during process. The following results were obtained:

| Length of Time of Foaming (Minutes) | Amount of Ibuprofen Dissolved |
| --- | --- |
| 5 | 0.26% |
| 15 | 0.28% |
| 25 | 0.31% |
| 35 | 0.34% |
| 45 | 0.32% |
| 55 | 0.34% |
| 65 | 0.39% |
| 75 | 0.37% |
| 85 | 0.37% |

Relatively little ibuprofen leached from the coated ibuprofen particles during the foaming process, indicating that this process was an excellent approach for minimizing the bitterness and throat burn associated with ibuprofen dosage forms that are chewed or dissolved in the mouth.

EXAMPLE 15

A foam with the following composition was prepared in an Oakes Foamer: water 269.98 g; glycerol 21.08 g; HPMC K3 35.72 g; HPMC E5 14.05 g; Genugel CJ 2.81 g; mannitol 126.46 g; Alpine Cream Flavor 5.62 g; vanilla 4.72 g; aspartame 6.30 g; coated ibuprofen 120.87 g. The following operating conditions were used in the equipment: Moter speed, 1000 rpm; rotor speed, 966 rpm; air flow rate, 100 cubic centimeters/minute; air pressure, 60 pounds per square inch (psig) back pressure, 31 psig.

The foam was dispensed into plastic weigh boats, and dried in an oven for two hours at 50 C. The dried foam tablets had a firm shape and dissolved in the mouth quickly.

EXAMPLE 16

Formation of Uniform Foam tabs by Molding

The following formulation was used in this example: water 200 g; glycerol 18 g; HPMC K3 24 g; HPMC E5 12 g; mannitol 100 g; vanilla 4 g; aspartame 4 g; coated acetaminophen 138 g.

Preparation took place in a Hobart mixer. Water was heated to about 42° C., and HPMC K3 and E5 were added while mixing at 200–500 rpm. Mixing was continued until the polymers had dissolved. Glycerin was then added while mixing continued. Mannitol, flavor, and aspartame were then added and mixing continued until a homogeneous mixture resulted. The mixture was cooled to about 35° C. Mixing speed was increased to greater than 2000 rpm to induce foaming. Polymer coated acetaminophen was added slowly, and mixing was continued until a thick foam occurred.

The foam was placed in cookie press. Foam was dispensed by weight into aluminum molds that were coated with a graphite impregnated Teflon film. The aluminum molds were chilled by storage at −80° C. until immediately before the foam was added to the molds. The amount of foam dispensed resulted in the foam protruding slightly above surface of the mold cavity. A roller coated with a non-stick surface was rolled over the surface of the molds. The roller compacted the foam so that it fit within the confines of the mold. The bottom of the filled molds was immediately exposed to liquid nitrogen to freeze the foam. This rapid freezing after dispensing minimized the coalescence of the bubbles and the collapse of the foam. After freezing, the foam tabs were released from the molds and placed on polyethylene terephthalate sheets that were coated with silicone. The sheets were placed in a forced air oven heated to 50° C. until the foam tabs were completely dry. This process resulted in foam tabs that were uniform in both shape and mass.

EXAMPLE 17

Foam Dosage Units Containing Acetaminophen and Conjugated Linoleic Acid

The following formulation was used in this example: Water 248.3 g, HPMC K3 29.8 g, HPMC E5 14.9 g, glycerin 22.3 g, mannitol 124.1 g, Red Dye #33 6 mg, D,L-malic acid 1.862 g, cherry trusil flavor #34443 2.48 g, aspartame 0.03 g, acesulfaine-K 0.93 g, sodium chloride 1.86 g, coated acetaminophen (Eurand) 173.2 g. Preparation took place in a Hobart mixer. Water was heated to about 42° C., and HPMC K3 and E5 were added while mixing at 200–500 rpm. Mixing was continued until the polymers had dissolved. Glycerin was then added while mixing continued. Mannitol, flavor, aspartame and acesulfame-K were then added and mixing continued until a homogeneous mixture resulted. The mixture was cooled to about 35° C.

Mixing speed was increased to greater than 2000 rpm to induce foaming. Polymer coated acetaminophen was added slowly, and mixing was continued until a thick foam occurred.

The foam was placed in cookie press. Foam was dispensed by weight into aluminum molds that were coated with a graphite impregnated TEFLON film. The foam was dried in a 50° C. oven for two hours.

The disk-shaped dried dosage forms were removed from the mold and inverted (i.e. the side of the dosage form that had been at the bottom of the mold was placed upright). Two hundred mg of conjugated linoleic acid (obtained from softgels provided by Pharnanutrients, Inc., Lake Bluff, Ill.) was added to the surface of individual disks. The conjugated linoleic acid was absorbed by the matrix of the dried foam within five minutes. The structure of the foam was not weakened by the addition of this oily material, and oily material did not leak from the disks. In contrast, when conjugated linoleic acid was added to the surface that had been the exterior surface of the disk during drying, little absorption of the oil occurred within five minutes, and a large portion of the added oil remained on the surface even after fifteen minutes.

We claim:

1. A method of preparing an edible comestible suitable for human consumption, comprising:
providing a polymeric foaming agent; optionally a non-cellulosic polysaccharide, a solvent and a therapeutically effective dose of a pharmaceutically active ingredient; admixing said polymeric foaming agent, non-cellulosic polysaccharide, solvent and pharmaceutically active ingredient; forming a foam dispersion from the admixed mixture; drying said foam dispersion to provide a dried foam with a density of less than about 0.40 grams/cubic centimeter.

2. The method of claim 1 wherein the pharmaceutically active material comprises particles that are covered with a taste masking coating.

3. The method of claim 1 wherein the foam dispersion is deposited in molds containing one or more cavities prior to drying.

4. The method of claim 3 wherein the deposited foam protrudes beyond the opening of the mold cavity, and the protruding foam is compressed to provide a surface flush with opening of the mold cavity.

5. The method of claim 4 wherein the foam dispersion is gravimetrically deposited in the mold cavity.

6. The method of claim 1 wherein the pharmaceutically active ingredient is selected from the group consisting of calcium carbonate, acetaminophen, ibuprofen, famotidine, naproxen, ketoprofen, pseudoephedrine, diphenhydramine, dextromethorphan, loratadine, and loperamide.

7. The method of claim 1 wherein the polymeric foaming agent is casein or hydroxypropylmethylcellulose.

8. A method of preparing an edible comestible suitable for human consumption, comprising dissolving a foaming agent in a solvent to yield a solution of said foaming agent, dispersing bubbles of gas in the foaming agent solution to yield a foam dispersion, drying said foam dispersion such that the dried foam dispersion has a bulk density of less than about 0.4 grams/cubic centimeter;

and adding a pharmaceutically active material or a nutritional material to the dried foam dispersion.

9. The method of claim 8 wherein the pharmaceutically active material is added to the dried foam dispersion in liquid form.

10. The method of claim 8 wherein the pharmaceutically active ingredient are neat liquids.

11. The method of claim 8 wherein the pharmaceutically active ingredient is melted prior to addition to the foam dispersion.

12. The method of claim 9 wherein the pharmaceutically active ingredient is nicotine and pharmaceutically acceptable salts of nicotine.

13. The method of claim 10 wherein the pharmaceutically active ingredient is nicotine.

14. The method of claim 8 wherein the liquid is a glycerol ester, a fatty acid ester, a polyglycerol ester, or a fatty acid.

15. The method of claim 14 wherein the fatty acid is conjugated linoleic acid, gamma linolenic acid, docosahexaenoic acid, or eicosapentaenoic acid.

16. The method of claim 11 wherein said pharmaceutically active ingredient is selected from the group consisting of phytosterols, phytostanols, esters of phytosterols, esters of phytostanols and oryzanol.

17. An edible comestible suitable for human consumption, comprising:

a polymeric foaming agent, a polysaccharide, and a pharmaceutically active ingredient; the comestible having a density of less than about 0.40 grams/cubic centimeter.

18. A method of preparing an edible comestible suitable for human consumption, comprising:

providing at least one polymeric foaming agent; a non-cellulosic polysaccharide, a solvent, and a pharmaceutically active material; admixing said polymeric foaming agent, a non-cellulosic polysaccharide and solvent to form a dispersion; entraining bubbles of gas in the dispersion to form a foam; and admixing said pharmaceutically active material with said foam; and drying said foam to provide a dried foam with a density of less than about 0.40 grams/cubic centimeter.

19. The method of claim 18 wherein the pharmaceutically active material comprises particles that are covered with a taste masking coating.

20. The method of claim 18 wherein the foam dispersion is deposited in molds containing one or more cavities prior to drying.

21. The method of claim 20 wherein the deposited foam protrudes beyond the opening of the mold cavity, and the protruding foam is compressed to provide a surface flush with opening of the mold cavity.

22. The method of claim 21 wherein the foam dispersion is gravimetrically deposited in the mold cavity.

23. The method of claim 18 wherein the pharmaceutical material is selected from the group consisting of calcium carbonate, acetaminophen, ibuprofen, naproxen, ketoprofen, pseudoephedrine, diphenhydramine, dextromethorphan, loratadine, and loperamide.

24. The method of claim 18 wherein the polymeric foaming agent is casein.

* * * * *